United States Patent
Cuny

(10) Patent No.: US 10,232,198 B2
(45) Date of Patent: Mar. 19, 2019

(54) METHOD FOR DETECTING A FALL OF A WORKER AND APPARATUS FOR DETECTING A FALL OF A WORKER

(71) Applicant: FALL—ALARMSYSTEM, Montbonnot-Saint-Martin (FR)

(72) Inventor: Arnaud Cuny, Saint Martin d'Uriage (FR)

(73) Assignee: FALL—ALARMSYSTEM, Montbonnot-Saint-Martin (FR)

( * ) Notice: Subject to any disclaimer, the term of this patent is extended or adjusted under 35 U.S.C. 154(b) by 0 days.

(21) Appl. No.: 15/800,620

(22) Filed: Nov. 1, 2017

(65) Prior Publication Data
US 2018/0117373 A1 May 3, 2018

(30) Foreign Application Priority Data
Nov. 3, 2016 (FR) ...................... 16 60614

(51) Int. Cl.
| | |
|---|---|
| *A61B 5/00* | (2006.01) |
| *A62B 35/00* | (2006.01) |
| *A61B 5/11* | (2006.01) |
| *G08B 21/04* | (2006.01) |
| *G08B 25/00* | (2006.01) |
| *G08B 25/01* | (2006.01) |

(Continued)

(52) U.S. Cl.
CPC ........ *A62B 35/0025* (2013.01); *A61B 5/1117* (2013.01); *A61B 5/7246* (2013.01); *G08B 21/043* (2013.01); *G08B 21/0446* (2013.01); *G08B 25/001* (2013.01); *G08B 25/014* (2013.01); *G08B 25/016* (2013.01); *G08B 25/08* (2013.01); *G08B 29/20* (2013.01); *A61B 2562/0219* (2013.01); *A63B 2220/18* (2013.01); *A63B 2220/40* (2013.01)

(58) Field of Classification Search
CPC ...... G08B 25/08; G08B 29/20; G08B 21/043; G08B 21/0446; G08B 25/001; G08B 25/014; G08B 25/016; A62B 35/0025; A61B 5/1117; A61B 5/7246
USPC ...................................................... 340/573.1
See application file for complete search history.

(56) References Cited

U.S. PATENT DOCUMENTS

| | | | |
|---|---|---|---|
| 8,773,269 B2 * | 7/2014 | Richardson | .......... A61B 5/0002 340/539.11 |
| 9,959,732 B2 * | 5/2018 | Xu | ....................... G08B 21/043 |

(Continued)

FOREIGN PATENT DOCUMENTS

| | | |
|---|---|---|
| WO | 16011507 A1 | 1/2016 |
| WO | 16075013 A1 | 5/2016 |

*Primary Examiner* — Kerri L McNally
(74) *Attorney, Agent, or Firm* — Thompson Coburn LLP; Steven M. Ritchey

(57) ABSTRACT

A method for detecting a fall of a worker attached to an anchor device includes steps for:
 a) measuring an orientation of a worker, using an orientation sensor with six axes on board a fall detection apparatus secured to the worker;
 b) calculating statistical properties representative of the measured orientation; and
 c) comparing statistical properties of reference values, a fall being considered to be detected only if the statistical properties correspond to the reference values according to predefined criteria, the comparison being done using an automatic classifier.

12 Claims, 3 Drawing Sheets

(51) Int. Cl.
*G08B 25/08* (2006.01)
*G08B 29/20* (2006.01)

(56) References Cited

U.S. PATENT DOCUMENTS

| | | | | |
|---|---|---|---|---|
| 2010/0176952 A1* | 7/2010 | Bajcsy | .................... | A61B 5/11 |
| | | | | 340/573.1 |
| 2016/0027279 A1* | 1/2016 | Ulner | ................ | G08B 21/0446 |
| | | | | 340/573.1 |
| 2018/0070889 A1* | 3/2018 | Lee | ....................... | A61B 5/1117 |

* cited by examiner

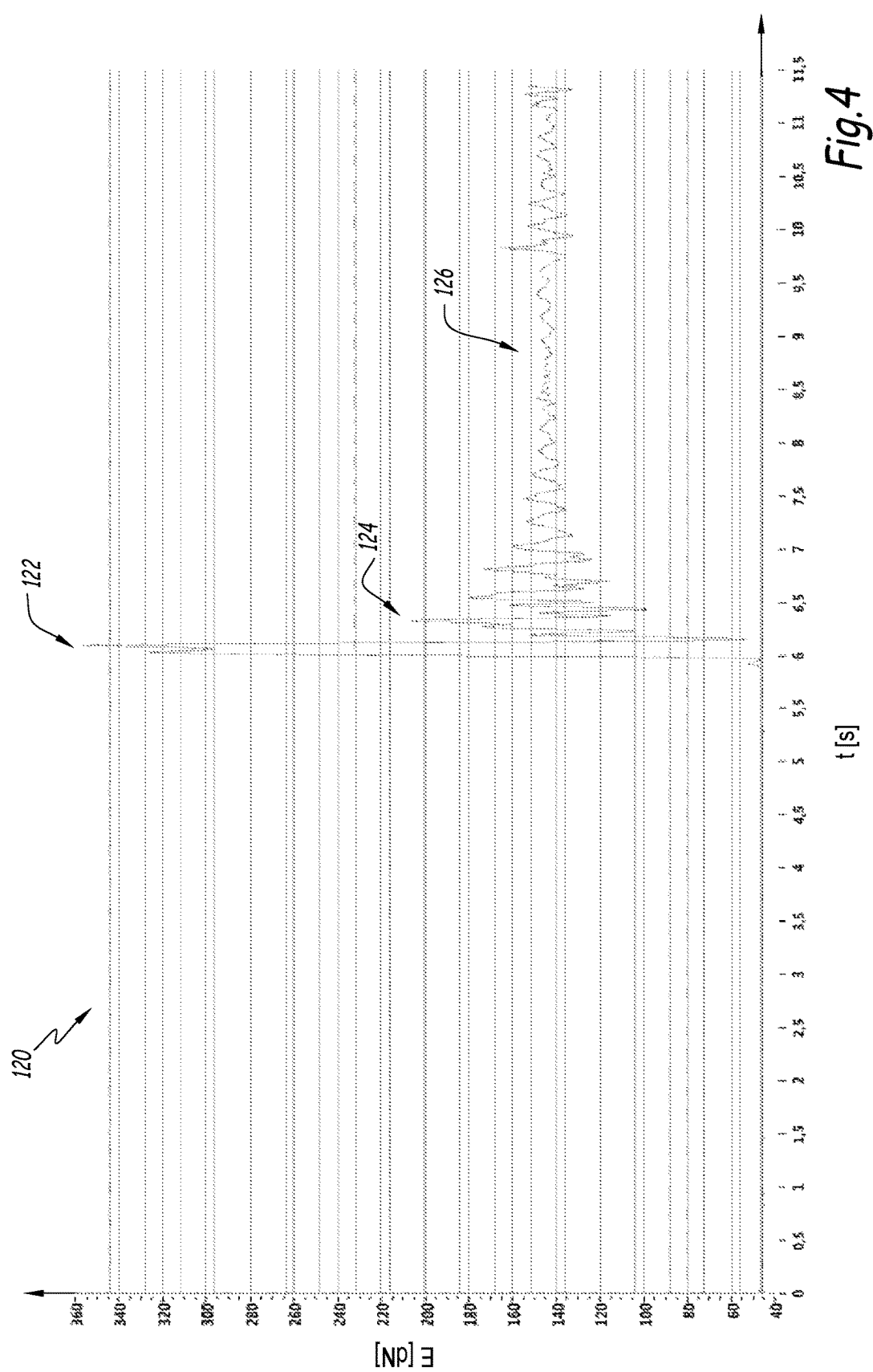

METHOD FOR DETECTING A FALL OF A WORKER AND APPARATUS FOR DETECTING A FALL OF A WORKER

CROSS-REFERENCE TO RELATED APPLICATIONS

The present application is a non-provisional application claiming the benefit of FR 1660614, filed Nov. 3, 2016, which is incorporated herein by reference in its entirety.

FIELD OF THE INVENTION

The present invention relates to a method for detecting a fall of a worker with a level change. The present invention also relates to an apparatus for detecting a fall of a worker.

BACKGROUND OF INVENTION

Fall detection apparatuses are known, referred to using the acronym IWAD (isolated worker alarm device) or IWP (isolated worker protection), which are intended to be worn by a worker and configured to detect a loss of verticality by this worker. When a loss of verticality is detected, these apparatuses are configured to trigger an alarm and contact a remote assistance center, so as to rescue the worker.

These known apparatuses are typically used by workers required to work alone, for example in industry, construction or merchandise transport.

These known apparatuses have the drawback of not making it possible to detect a fall with a level change, or to differentiate between an accidental fall, for which assistance must be provided to the worker, and a controlled fall, in which no assistance is necessary. An example controlled fall is when a worker jumps on purpose from a low height, for example a stepladder or a truck cab. Thus, these apparatuses incur the risk of not detecting a real fall, when they needlessly trigger false positives.

Apparatuses are also known described in documents US 2006/282021 A1, US 2012/119904 A1, US 2006/049950 A1 and FR 2785073 A1.

SUMMARY OF INVENTION

The invention more particularly aims to resolve these drawbacks by proposing a method and apparatus for detecting a fall with a level change, with increased reliability, in particular by reducing the risk of false positives.

To that end, the invention relates to a method for detecting a fall with a level change of a worker attached to an anchor device according to claim 1.

Owing to the invention, the detection of a fall from a height by a worker is done with increased reliability, in particular when this worker is suspended from an anchor device.

Indeed, in the known apparatuses, the detection of the fall is based on a verticality measurement of the worker's body, the worker being considered to have fallen when verticality is lost, i.e., he no longer occupies a vertical position, for example because he is lying on the ground.

Such detection is not reliable when the worker is attached to an anchor device, since in this case, the worker can retain an essentially vertical position even after having fallen with a level change.

By detecting the fall conditions from reference data using the classifier, the likelihood of detecting a fall is higher, even when the worker is not in a loss of verticality position at the end of his fall. Furthermore, this makes it possible to reduce false positives, i.e., the incorrect detection of falls when the worker performs a controlled movement, such as a jump.

According to advantageous but optional aspects of the invention, such a method may incorporate one or more of the features of the dependent claims 2 to 12, considered alone or according to any technically allowable combination.

According to another aspect, the invention relates to an apparatus for detecting a fall with a level change of a worker attached to an anchor device, this apparatus being according to claim 13.

BRIEF DESCRIPTION OF THE DRAWINGS

The invention will be better understood and other advantages thereof will appear more clearly in light of the following description of a method and an apparatus for detecting a fall, provided solely as a non-limiting example and done in reference to the appended drawings.

FIG. 4 is a schematic illustration of a signal acquired by the detection apparatus of FIG. 1 during the fall of a worker attached to an anchor device.

DETAILED DESCRIPTION OF INVENTION

Figure 1:
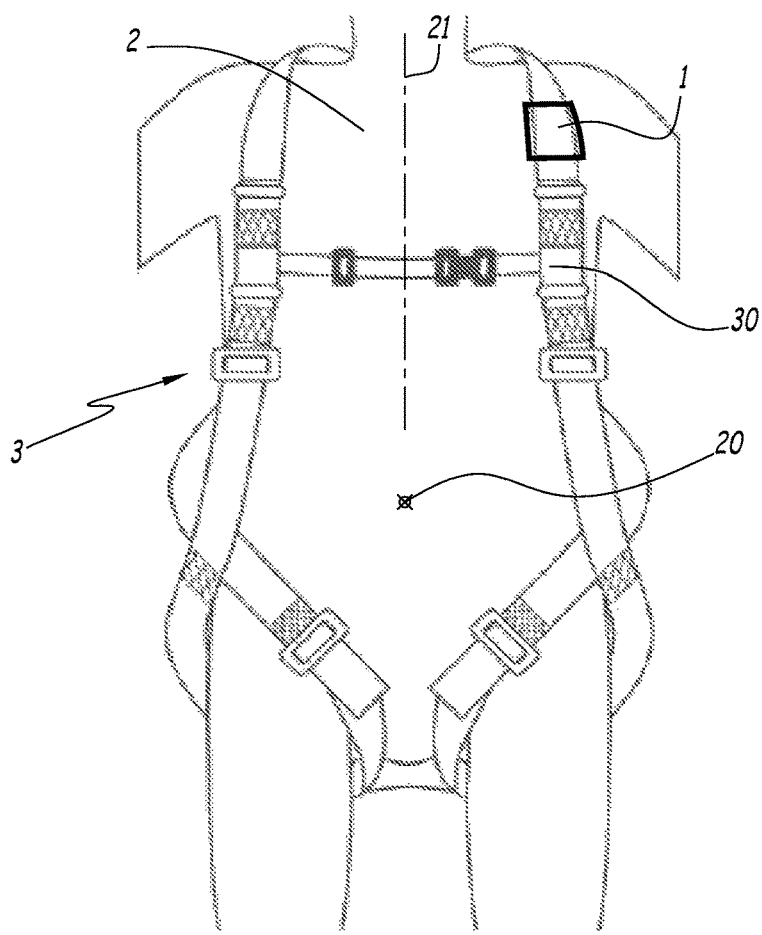
FIG. 1 is a schematic illustration of an apparatus according to the invention for detecting a fall with a level change of a worker.

FIG. 1 schematically shows an apparatus 1 for detecting a fall of a human worker 2.

For example, the worker 2 is provided with a safety harness 3 that is attached to an anchor device via a fall prevention apparatus, not illustrated. The attachment of the fall prevention apparatus to the safety harness 3 can be sternal or dorsal, for example using a carabiner.

In a known manner, an anchor device can be stationary or mobile. The fall prevention apparatus is used to hold the worker 2 in case of accidental fall, in particular during a fall with a level change, i.e., a fall from a height. The fall prevention apparatus is for example a rope, a metal cable or a chain.

The safety harness 3 here includes straps 30, for example made from a textile, that are positioned and tightened around the body of the worker 2.

Reference "20" denotes the center of gravity of the worker 2, and "21" denotes a longitudinal axis of the worker 2. The axis 21 here is oriented along a vertical direction when the worker 2 is standing in an upright position.

The apparatus 1 is programmed to detect an accidental fall of the worker 2. The apparatus 1 is further programmed so as, when a fall is detected, to trigger an alarm, as explained below.

Figure 2:
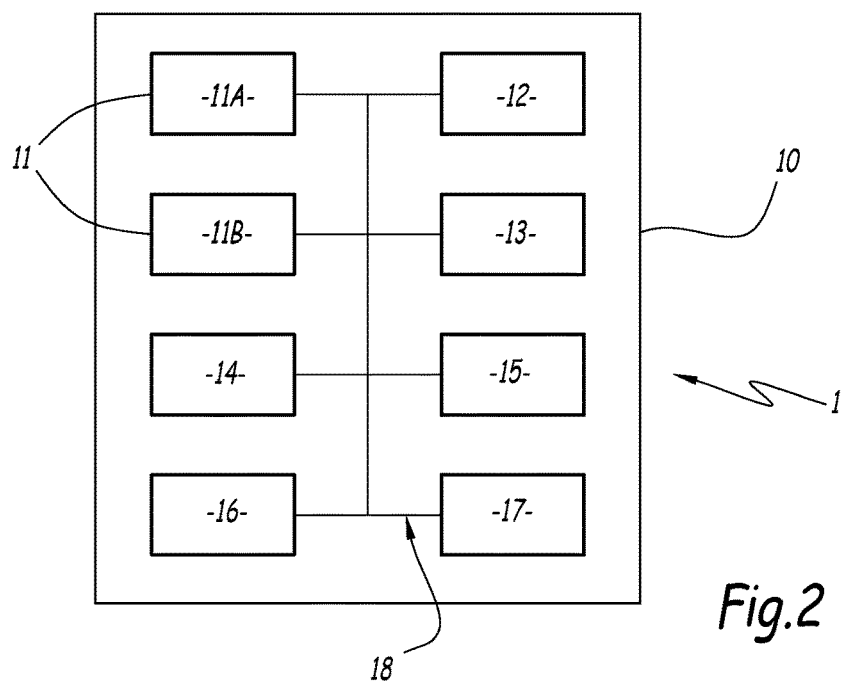
FIG. 2 is a schematic illustration of the detection apparatus of FIG. 1.

As illustrated in FIG. 2, the apparatus 1 includes an orientation sensor 11 with six axes, or inertial unit, that includes an accelerometer 11A with three axes and a gyroscope 11B with three axes. The sensor 11 is suitable for measuring an orientation of the worker 2.

The sensor 11 may include the accelerometer 11A and the gyroscope 11B either as separate components, or as a same component suitable for implementing these two functionalities.

The accelerometer 11A is suitable for measuring a movement by the worker 2, for example by measuring an acceleration of the worker 2, along three orthogonal geometric axes in a first reference coordinate system. These reference axes are not necessarily aligned with the axis 21 of the worker 2.

The gyroscope 11B is suitable for measuring an instantaneous angular position of the worker 2 relative to three orthogonal geometric axes of a second reference coordinate system. For example, the first and second reference coordinate systems correspond to a same reference coordinate system of the sensor 11.

The sensor 11 is thus suitable for measuring, at each moment, three angular position components associated with the three axes of the first coordinate system and three acceleration components of the worker 2 associated with the three axes of the second coordinate system. The sensor 11 provides, on an output interface, measuring signals, representative of these measurements.

As an illustration, in this example, the sensor 11 is the sensor marketed by the company STMICROELECTRONICS under reference LSM6DS3.

The use of a sensor with six axes makes it possible to measure the orientation of the worker 2 with better precision and to increase the reliability of the method for detecting a fall.

The apparatus 1 also includes a programmable electronic computing unit 12, a memory 13 and a man-machine interface 14.

Figure 3:
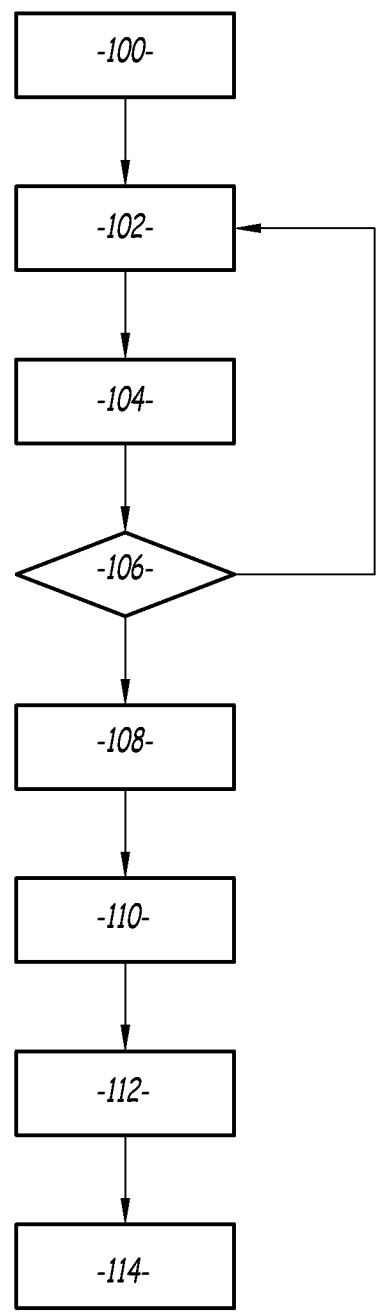
FIG. 3 is a flowchart of a method for detecting a fall of a worker from a height according to the invention.

The computing unit 12 here is a microprocessor or a programmable microcontroller. The unit 12 is in particular programmed to carry out instructions stored in the memory 13 in order to carry out the method for detecting a fall of a worker 2 as illustrated in FIG. 3.

For example, the memory 13 includes a non-volatile memory module, here using Flash or EEPROM technology.

The man-machine interface 14 is in particular suitable for displaying the state of the apparatus 1, for example the state of a datalink or the charge level of a power source or to display an alarm emitted by the apparatus 1. The man-machine interface 14 is also suitable for allowing the worker 2 to intervene during the performance of the detection method, for example to interrupt an alarm signal if a fall is detected, as explained later.

For example, the man-machine interface 14 includes lighted indicators, such as light-emitting diodes, pushbuttons and/or switches. Alternatively, the man-machine interface 14 includes a touch-sensitive screen.

The apparatus 1 advantageously includes a telecommunications interface 17 as well as a microphone 15 and a speaker 16.

The telecommunications interface 17 is suitable for establishing a wireless datalink with a remote computer server, for example via a wireless telephony network or the Internet. Here, the telecommunications interface 17 is compatible with the GSM, UMTS and LTE wireless telephony technologies. For example, the telecommunications interface 17 contains a radio antenna.

Advantageously, the interface 17 makes it possible to send data measured by the sensor 11 to the remote computer server.

The apparatus 1 is further advantageously programmed to establish voice communication between the worker 2 and a remote operator if an alarm is triggered after a fall is detected, such that the worker 2 can transmit information on his condition by voice, using the microphone 15. The remote operator can also listen to what is happening even if the worker 2 does not respond.

Alternatively, the microphone 15 and the speaker 16 can be replaced by a coaxial audio connector, for example of the audio jack type. The voice communication is then done using a headset and microphone worn by the worker 2 and connected to the apparatus 1 via this connector.

The speaker 16 is also suitable for emitting a sound alarm signal audible by the worker 2.

The apparatus 1 also includes a data bus 18, connected to the components of the apparatus 1, here to the sensor 11, the unit 12, the memory 13, the interface 14, the microphone 15, the speaker 16 and the telecommunications interface 17, to allow data to be exchanged between these components. According to one illustrative example, the database 18 is a wired link, formed by electrically conducting tracks arranged on a printed circuit.

The apparatus 1 further includes a housing 10, preferably made from a rigid material and withstanding impacts, inside which the other components of the apparatus 1 are housed. The man-machine interface 14 is at least partially accessible to the worker 2 from outside the housing 10.

In this example, the housing 10 is provided, on an outer face, with fastening means intended to secure it to one of the straps 30, such as a hook or a strip of self-adhesive material, for example of the Velcro® type, suitable for being attached to a complementary surface of the strap 30 of the safety harness 3.

The apparatus 1 is intended to be secured to the worker 2, preferably above the center of gravity 20. In this example, the apparatus 1 is securely attached on a strap 30 of the safety harness 3.

Advantageously and optionally, the apparatus 1 is placed at chest level for the worker 2. In this way, the measurements acquired by the sensor 11 are more representative of the position of the worker 2, which increases the detection reliability. This also allows the worker 2, when a remote communication is established after an alert, to communicate more easily with the remote operator using the microphone 15 and speaker 16, the latter then being closer to the head of the worker 2.

The apparatus 1 further includes an electrical power supply system, not illustrated, such as a battery of rechargeable electric storage cells, suitable for supplying electricity to the apparatus 1 during operation thereof.

Advantageously, the apparatus 1 includes a data connector, for example of the USB (Universal Serial Bus) type, which is connected to the data bus 18 and which is accessible from outside the housing 10. The connector makes it possible to exchange data between the apparatus 1 and a central unit, not illustrated, for example to load data in the memory 13.

For example, identification data relative to the worker 2 is sent to the memory 13 from the central unit using this connector. This is particularly useful when several workers 2 are led to use a same apparatus 1 in series, one after another. In this way, the apparatus 1 is connected to the central unit before being assigned to a worker, to update the identification data.

Particularly advantageously, the connector is suitable for allowing recharging of the electrical supply system when it is connected to the central unit.

Alternatively, the interface 17 is further advantageously configured to establish a short-range data exchange link, for example of the Bluetooth® type, to exchange such data with the central unit.

Optionally, the apparatus 1 further includes a geolocation module, here connected to the data bus 18. For example, this geolocation module is suitable for working with a geolocation system of the GPS (Global Positioning System) type.

In this illustrative example, the apparatus 1 is an electronic apparatus dedicated to the fall detection function.

Alternatively, the apparatus 1 is a generic mobile communication terminal, for example of the tablet or smartphone type, which is programmed to carry out the fall detection functions. For example, a dedicated executable application is downloaded, from a remote computer server or from a removable data recording medium such as a memory card, then is installed in the memory 13, so as to be able to be executed by an operating system of the communication apparatus.

The computing unit 12 is in particular programmed to acquire the orientation values measured by the inclined sensor 11 and to calculate the statistical properties representative of the measured orientation values.

For example, the statistical properties are chosen, for each axial component of the movement and angular position that are measured by the sensor 11, from among the set made up of:
- the minimum value;
- the maximum value;
- the difference between the maximum value and the minimum value;
- the maximum of the absolute value of the first difference, the first difference being defined as being equal to the difference between two consecutive values of this component;
- the deviation between the maximum and the minimum of the first difference;
- the variance;
- the asymmetry, or skewness;
- the kurtosis;
- the synchrovariance, defined as the difference between the largest variance value and the smallest variance value irrespective of the geometric axis; and
- the difference between the largest value and the smallest value of the maximum of the absolute value of the first difference, irrespective of the geometric axis.

Preferably, at least five of the above statistical properties are used, still more preferably, all of the above statistical properties are used.

For example, these statistical properties are calculated by the computer 12 for each of the three angular position axial components associated with the three axes of the first coordinate system and the three acceleration axial components associated with the three axes of the second coordinate system, from corresponding values measured, continuously or repeatedly, during a predefined duration.

Preferably, here, the measurements are done during a predefined time range, for example with a duration equal to 1 second. The representative statistical properties are next calculated at the end of this time range, from values measured during this predefined time range. For example, the values measured by the sensor 11 for successive moments are stored as they are acquired in a first dedicated area of the memory 13 until the end of the time range.

Furthermore, each time range here is divided into several predefined time intervals, here each lasting 250 ms. At the end of each interval, a new time range is initiated, in parallel with the existing time range.

For example, the values measured by the sensor 11 for successive moments are stored as they are acquired in a second dedicated area of the memory 13, separate from the first area, until the end of this second time range. In parallel, the measured values continue to be stored in the first memory area until the end of the previous time range.

Thus, the detection apparatus 1 is suitable for acquiring orientation measurements of the worker 2 and analyzing them to detect the occurrence of a fall in parallel for several time ranges that intersect one another at least partially in pairs.

The analysis of the calculated statistical properties to detect the fall of the worker 2 is done here by the unit 12 using an automatic classifier, which receives the calculated statistical properties as input. Here, this analysis is done independently for each of the predefined time ranges.

In this example, the classifier is based on the "random decision forest" method, including a set of decision trees.

The classifier is driven beforehand from reference data, as explained below. The decision trees making up the forest are automatically built from reference data during a learning phase of the classifier.

For each time range, the statistical properties calculated for each of the six components previously described are stored in an input vector, which is provided at the input of the classifier.

The decision trees are suitable, in response to this input vector, for classifying this input vector in one or the other of two predefined classes, one associated with a suspected fall and the other associated with a suspected absence of fall. This classification includes comparing calculated statistical properties with reference values.

The fall is said to be detected only if the calculated statistical properties correspond to the reference values according to the predetermined criteria.

The reference values and the predetermined criteria are a function of the reference data with which the classifier has previously been driven.

In this example, the comparisons are done by a decision algorithm as a function of the decision trees, the fall being said to be detected only if the majority of the decision trees from the forest of trees have classified the corresponding input vector in the class associated with the suspected fall.

For example, the forest includes twenty decision trees with a maximum depth greater than or equal to five or ten, and preferably less than or equal to 53.

The driving of the classifier is done here from reference data acquired from the apparatus 1 used in controlled tests, for which the calculated statistical properties are associated with certainty with a fall situation, or on the contrary, absence of fall situation.

In this example, the tests were done with a mannequin representative of a worker 2 and on which the apparatus 1 is fastened in a manner similar to that described above. This mannequin is provided with a safety harness 3 attached to an anchor device. The mannequin next undergoes several falls intended to simulate actual falls and during which the apparatus 1 uses the sensor 11 to record the orientation of the mannequin in the same manner as it would do for a worker 2. Several fall configurations are reproduced, each time modifying one or several fall parameters, for example modifying:
- the direction of the fall: forwards, sideways, backwards;
- the attachment of the safety harness 3 to the fall prevention apparatus in a ventral or dorsal manner;
- the nature of the fall prevention apparatus and its mechanical state at the time of the fall, for example free length or mechanical tension; and/or
- the mechanical components used to connect the fall prevention apparatus to the safety harness 3 and to the anchor device: single or double safety strap, presence or absence of an energy absorber, fall prevention on belaying support, fall prevention with automatic recall.

Preferably, several falls, for example five, are done for each combination.

Furthermore, several controlled fall simulations are done, for example by equipping a worker 2 with the apparatus 1 and causing him to perform controlled falls, for example jumping from a stepladder or a stair. The measurements from the sensor 11 are then recorded and the associated statistical properties are calculated.

The classifier is then driven from this reference data.

One example embodiment of a method for detecting a fall of the worker 2 according to the invention is now described in reference to flow chart of FIG. 3.

Preferably, during a prior step 100, a classifier previously driven is acquired by the apparatus 1. For example, the reference values and the corresponding predefined rules are acquired and stored in the memory 13.

Next, during a step 102, the orientation of the worker 2 is measured using the sensor 11. This measurement is done continuously or for successive moments over time during the time range. For example, as previously indicated, the measurements from the sensor 11 are used for several separate time ranges and intersect one another in pairs.

Next, during a step 104, all or some of the statistical properties previously described and representative of the measured orientation values are calculated by the electronic computing unit 12. This calculation is done independently at the end of each time range, from values measured during this time range.

Then, during a step 106, the calculated statistical properties are compared with predefined reference values. The comparison is done using the automatic classifier previously described and the electronic computing unit 12. A fall is considered to be detected only if the statistical properties correspond to the reference values. Otherwise, no fall is considered to be detected for this time range.

When no fall is detected at the end of step 106, the computing unit 12 automatically analyzes the values measured during the following time range. Step 106 is thus carried out successively for each time range at the end of each implementation of step 104.

Owing to the invention, the detection of a fall by a worker from a height is done with increased reliability, in particular when this worker is suspended from an anchor device.

Indeed, in the known apparatuses, the detection of the fall is based on a verticality measurement of the worker's body, which is not reliable if the worker 2 retains an essentially vertical position even after having fallen.

In particular, experimental tests have shown that at the end of such a fall and when the worker 2 is attached to the anchor device, the axis 21 has an angle relative to the vertical that is less than or equal to 60°, preferably less than or equal to 56°.

Advantageously, when a fall is detected at the end of step 106, then, during step 108, a confirmation request is sent to the worker 2. This request includes the sending of a signal by the apparatus 1 to the worker 2, for example a sound signal emitted using the speaker 16 and/or an optical signal emitted on the man-machine interface 14. This confirmation request also includes triggering a countdown of the elapsed time by the computing unit 12.

The detected fall is considered to be confirmed if no acknowledgment signal from the worker 2 is received by the man-machine interface 14 within a predefined length of time, for example from the moment when the fall is detected.

The acknowledgment signal is for example sent by the worker 2 by pressing a button on the man-machine interface 14.

Otherwise, if an acknowledgment signal from the worker 2 is received by the man-machine interface 14 within the predefined length of time, then the detected fall is considered to be a false positive and is not taken into account. The apparatus 1 then continues to carry out steps 102, 104 and 106 over the following time ranges.

Steps 102, 104 and 106 continue to be carried out for successive time ranges for example until the apparatus 1 is stopped or until a fall is detected at the end of step 106, or advantageously after confirmation during step 108.

Advantageously, if a fall is confirmed at the end of step 108, then the apparatus 1 automatically triggers an alarm. This triggering for example includes emitting an alert signal toward a remote computer server, using the telecommunications interface 17. This triggering may also include emitting a sound signal via the speaker 16.

When step 108 is omitted, step 110 may also be carried out directly if a fall is detected at the end of step 106.

Then, optionally, during step 112, a voice communication is established between the apparatus 1 and a remote operator. For example, a telephone communication is established using the telecommunications interface 17 toward a dedicated assistance center.

This telephone call here is initiated by the apparatus 1, by contacting a predefined telephone number. Alternatively, the telephone call may be initiated by a remote server upon receiving the alarm signal by selecting a recipient from among a predefined list of contacts to be reached in case of emergency, based on the identifier of the worker 2.

In this way, the worker 2 can, if he is conscious, communicate by voice with the remote operator, using the microphone 15 and the speaker 16, to confirm his condition, and in particular to confirm whether he has actually fallen. Based on the response from the worker 2, the remote operator orders help to be sent, or alternatively, orders the alarm to be stopped if no fall has occurred.

Optionally, if the detected fall is confirmed as corresponding to an actual fall, then during step 114, the data measured by the sensor 11 is sent automatically, by the telecommunications interface 17, to the remote computer server. For example, this data is used to update the database of reference data in order to build a new version of the random forest.

In this way, the classifier is updated and enriched by the remote server, by adding data associated with a fall considered to be verified to the reference data.

Optionally, other information can be sent to the remote server, for example using the interface 17, such as an identifier of the worker 2, the date and time of the fall, the triggering of the alarm and, if applicable, reception of an acknowledgment signal.

According to one alternative, the spatial coordinates of the worker 2 are measured by the geolocation module and the corresponding position is sent automatically to the remote server, using the interface 17. The latter is then programmed to display the corresponding position of the worker 2 on a map. Thus, the position of the worker 2 can be tracked in real time. This is particularly advantageous when the worker 2 is called upon to move in a very large industrial site.

According to another alternative, the apparatus 1 is suitable for communicating with a similar apparatus 1. The apparatuses 1 are in particular programmed to trigger an alarm when they are separated from one another by a distance exceeding a predefined distance. The distance is for example measured in real time by the computing units 12 and using respective geolocation modules of the two apparatuses 1.

This is particularly advantageous to prevent two workers 2 having to work jointly from accidentally being separated after having lost sight of one another, for example when they move around a very large industrial site, such as a steel factory.

This last variant can be implemented independently of the fall detection method.

In general, the apparatus 1 is more particularly programmed to detect an accidental fall with a level change of the worker 2 when this worker 2 is attached to the anchor device, the latter preventing the worker 2 from hitting the ground. In other words, at the end of the fall, the worker 2 is suspended in the air by his fall prevention apparatus.

For example, when the user 2 falls with a level change while attached to the anchor device, his fall is broken down into several phases, during which the worker 2 undergoes a movement different from that experienced during the other phases.

The fall begins with a first so-called acceleration phase, during which the worker 2 is in freefall. This fall can be accompanied by a twisting movement of the body of the worker 2.

Next, during a second phase, the fall stops abruptly, under the action of the anchor device to which the worker 2 is attached, here owing to the fall prevention apparatus and the harness 3.

Lastly, during a third phase, the worker 2 remains suspended in the air owing to the fall prevention apparatus, and experiences oscillating movements that tend to lessen with time.

Such a fall is therefore different from a fall on one's feet by a person walking on the ground. In a fall from a standing position, the person experiences an impact with the ground. In the case of a fall with a level change by a worker attached to an anchor device, the worker does not experience an impact with the ground. He does, however, experience an abrupt stop in movement when the fall prevention apparatus is activated to retain him, but this movement is different from an impact with the ground. The worker 2 is stopped mid-fall without touching the ground. The movements and accelerations experienced by the worker 2 during a stop mid-fall, as measured by the sensor(s) 11 of the apparatus 1, are different from those experienced during a fall with an impact on the ground.

In other words, the fall of the worker 2 has a particular signature.

FIG. 4 shows an example of a signal 120 acquired by the apparatus 1 when the worker 2 falls with a level change while being attached to the anchor device, with no impact with the ground.

This signal 120 is for example representative of an acceleration experienced by the worker 2 measured from the sensor 11 along one of the axes. This signal 120 here is expressed as a force "E" expressed in Newton, as a function of time "t" expressed in seconds.

The signal 120 here includes three consecutive regions 122, 124 and 126. In this illustrative example, the worker 2 remains immobile prior to the fall.

The first region 122 corresponds to the first phase previously described, i.e., freefall. It includes one or several heightened intensity peaks.

The second region 124 corresponds to the second phase previously described, i.e., stopping of the fall. It includes one or several intensity peaks substantially less high than the intensity of the peaks in the first region 122.

The third region 126 corresponds to the third phase previously described, i.e., to the oscillating movement absorbed by the worker 2 suspended from the anchor device.

Thus, the apparatus 1 is advantageously programmed, in particular through the electronic computing unit 12 and executable instructions contained in the memory 13, to detect the fall from the measured orientation, taking into account the different phases previously defined of the fall by the worker 2.

For example, during step 104, the statistical properties are calculated from one or several portions of the measuring signals of the orientation of the worker 2 as measured by the sensor 11, each signal portion being representative of a phase of the fall of the worker 2.

For example, each measured axial component of the movement and of the angular position assumes the form of a measurement signal, here delivered by the sensor 11. For each axial component of the movement and angular position, i.e., for each measurement signal, the chosen statistical properties are calculated for several portions of the corresponding signal and/or for several combinations of portions of the corresponding signal, each of these portions of signals being associated with one of the phases of the fall as previously defined.

Advantageously, the apparatus 1 is programmed to identify automatically, for a given measurement signal, the portions corresponding to phases of the fall, for example based on a predefined definition.

The calculation of the chosen statistical properties can for example be done separately for each portion of a same measurement signal, or be done for several portions of a same measurement signal corresponding to different phases of the fall of the worker 2, or be done for several portions of different measurement signals, but corresponding to a same phase of the fall.

During step 106, the comparison is done taking the phases of the fall into account. For example, the obtained reference values, here obtained by learning, themselves take these phases of the fall into account.

The embodiments and alternatives and embodiments considered above may be combined to create new embodiments.

What is claimed is:

1. A method for detecting a fall of a worker attached to an anchor device, the method comprising:
   a) measuring an orientation of a worker, using an orientation sensor with six axes to measure a movement along three geometric axes of a first coordinate system and to measure an angular position relative to three geometric axes of a second reference coordinate system, this orientation sensor being on board a fall detection apparatus secured to the worker;
   b) calculating statistical properties representative of the measured orientation, this calculation being done by an electronic computing unit of the fall detection apparatus; and
   c) comparing statistical properties of reference values, a fall being considered to be detected only if the statistical properties correspond to the reference values according to predefined criteria, the comparison being done using an automatic classifier implemented by the electronic computing unit;

wherein, during step a), orientation values are measured during a predefined time range, wherein during step b), the representative statistical properties are calculated from values measured during the predefined time range, and in that steps a), b) and c) are carried out by the detection apparatus for several predefined time ranges that intersect one another at least partially in pairs.

2. The detection method according to claim 1, wherein the statistical properties calculated during step b) are chosen, for each axial component of the movement and angular position measured by the sensor, from among the set made up of the minimum value, the maximum value, the difference between the maximum value and the minimum value, the maximum of the absolute value of the first difference, the deviation between the maximum and the minimum of the first difference, the variance, the skewness, the kurtosis, the synchrovariance defined as the difference between the largest variance value and the smallest variance value irrespective of the geometric axis and the difference between the largest value and the smallest value of the maximum of the absolute value of the first difference irrespective of the geometric axis.

3. The detection method according to claim 1, wherein during step c), the classifier implemented by the computing unit to perform the comparison is a random forest comprising decision trees, the decision trees having been built beforehand from reference data during a prior learning phase of the classifier, the reference values and the predefined criteria depending on reference data, the reference data being acquired from the detection apparatus during control tests, for which the calculated statistical properties are associated with certainty with a fall situation, or on the contrary, an absence of fall situation.

4. The detection method according to claim 1, wherein the orientation sensor includes an accelerometer with three axes and a gyroscope, and wherein, during step a), the movement along the three geometric axes is measured by the accelerometer and the angular position relative to these three geometric axes is measured by the gyroscope.

5. The detection method according to claim 1, wherein, during step a), the orientation sensor of the detection apparatus is kept attached to the worker while being placed above the center of gravity of the worker.

6. The detection method according to claim 1, wherein, if a fall is detected at the end of step c), the method further comprises:
   d) requesting confirmation from the worker, including a emitting a signal via the apparatus intended for the worker, the detected fall being considered to be confirmed if no acknowledgment signal from the worker is received by a man-machine interface of the apparatus within a predefined length of time, the detected fall being considered to be a false positive if an acknowledgment signal from the worker is received by the man-machine interface within the predefined length of time.

7. The detection method according to claim 1, further comprising triggering, by the detection apparatus, of an alarm when a fall is detected.

8. The detection method according to claim 1, further comprises sending calculated statistical properties to a remote computer server when a fall is detected, this transmission being done using a telecommunications interface of the detection apparatus.

9. The detection method according to claim 1, wherein the fall of the worker is a fall with a level change in which the worker is prevented from striking the ground owing to the anchor device.

10. The detection method according to claim 1, wherein, during step b), the statistical properties are calculated from one or several portions of the measuring signals of the orientation of the worker as measured by the movement sensor, each signal portion being representative of a phase of the fall of the worker.

11. The detection method according to claim 2, wherein, during step b), each measured axial component of the movement and angular position assumes the form of a measurement signal and wherein, for each axial component of the movement and angular position, i.e., for each measurement signal, the chosen statistical properties are calculated for several portions of the corresponding signal and/or for several combinations of portions of the corresponding signal, each of these portions of signals being associated with one of the phases of the fall.

12. An apparatus for detecting a fall of a worker attached to an anchor device, this apparatus being intended to be secured to the worker, the apparatus comprising:

a movement sensor with six axes to measure a movement along three geometric axes of a first coordinate system and to measure an angular position relative to three geometric axes of a second reference coordinate system;

a programmable electronic computing unit programmed to:

a) measure an orientation of the worker, using the movement sensor;

b) calculate statistical properties representative of the measured orientation values; and c) compare statistical properties of reference values, a fall being considered to be detected only if the statistical properties correspond to the reference value intervals according to predefined criteria, the comparison being done using an automatic classifier;

wherein, during step a), orientation values are measured during a predefined time range, wherein during step b), the representative statistical properties are calculated from values measured during the predefined time range, and in that steps a), b) and c) are carried out by the detection apparatus for several predefined time ranges that intersect one another at least partially in pairs.

* * * * *